United States Patent
Gotoh (10) Patent No.: US 7,220,052 B2
(45) Date of Patent: May 22, 2007

(54) X-RAY DIAGNOSTIC APPARATUS (75) Inventor: Atsushi Gotoh, Kuroiso (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/684,377

(22) Filed: Oct. 15, 2003

(65) Prior Publication Data

US 2004/0081285 A1    Apr. 29, 2004

(30) Foreign Application Priority Data

Oct. 16, 2002 (JP) ............................. 2002-301937

(51) Int. Cl.
*H05G 1/02* (2006.01)

(52) U.S. Cl. .................. 378/193; 378/195; 378/197

(58) Field of Classification Search ............. 378/193, 378/195–198
See application file for complete search history.

(56) References Cited

U.S. PATENT DOCUMENTS

| 5,960,054 | A | * | 9/1999 | Freeman et al. | ................ | 378/4 |
| 6,155,713 | A | * | 12/2000 | Watanabe | ................... | 378/197 |
| 6,435,713 | B1 | * | 8/2002 | Iizuka | ......................... | 378/195 |

* cited by examiner

*Primary Examiner*—Edward J. Glick
*Assistant Examiner*—Jurie Yun
(74) *Attorney, Agent, or Firm*—Oblon, Spivak, McClelland, Maier & Neustadt, P.C.

(57) ABSTRACT

An X-ray diagnostic apparatus includes two photographic systems, a control circuit controlling a movement of the second photographic system. A control circuit which controls movement of a photography system can move the photographic system to a temporary evacuation position closer to a photography position than an evacuation position, according to an instruction from an operator.

19 Claims, 5 Drawing Sheets

X-RAY DIAGNOSTIC APPARATUS

CROSS-REFERENCE TO RELATED APPLICATIONS

This application is based upon and claims the benefit of priority from the prior Japanese Patent Application No. 2002-301937, filed Oct. 16, 2002, the entire contents of which are incorporated herein by reference.

BACKGROUND OF THE INVENTION

1. Field of the Invention

The present invention relates to a biplane type X-ray diagnostic apparatus enabling photographing (fluoroscopic imaging/radiographic imaging) in two directions.

2. Description of the Related Art

A biplane type X-ray diagnostic apparatus developed chiefly for use in circulatory system examinations is equipped with two photographic (fluoroscopic/radiographic) systems in order to achieve simultaneous photographing in two directions: one is a frontal photographic system that photographs a subject laid on his back on the diagnostic table top in the frontal plane, and the other is a lateral photographic system that photographs the subject in the lateral plane. The frontal photographic system includes an X-ray tube and an X-ray detector respectively attached to the both ends of a C-arm supported by a floor-standing stand. The lateral photographic system also includes an X-ray tube and an X-ray detector, which are respectively attached to the both ends of an Ω-arm suspended from the ceiling.

Because the stand is installed to the floor, the C-arm in the frontal system is allowed to swivel about the stand (strut rotation), but in principle, remains immovable with respect to the floor surface. On the other hand, the Ω-arm in the lateral system is attached to the strut suspended from a slider engaged with a rail laid on the ceiling, and is therefore provided movably along the rail. This arrangement enables single-plane photographing with the use of the frontal photographic system alone by retracting the lateral photographic system to a remote place.

In the case of a diagnostic of a cardiac region, the blood vessel formation or injection of an anti-cancer agent through a catheter manipulation by X-ray fluoroscopy, or IVR (interventional radiology) accompanying an operation, such as occlusion of the vessels of nutrition to tumor tissues, biplane photographing using both the frontal and lateral photographic systems and single-plane photographing using the frontal photographic system alone are switched over frequently.

The lateral photographic system needs to be retracted from a photographing position to an evacuation position and returned to the photographing position from the evacuation position each time the switching takes place. Moreover, in order to avoid the interference with operations of the frontal photographic system by the lateral photographic system at the evacuation position and to secure a sufficiently large working space for an operator, the evacuation position is set to a place as far as 3 m away from the photographing position. Hence, each time biplane photographing and single-plane photographing are switched over, an examination or an operation work is halted for not short a time needed to move the lateral photographic system between the photographing position and the evacuation position, and the work efficiency is deteriorated as a result.

BRIEF SUMMARY OF THE INVENTION

The object of the invention is therefore to shorten a stand-by time associated with the switching between biplane photographing and single-plane photographing in a biplane type X-ray diagnostic apparatus.

According to an aspect of the invention, an X-ray diagnostic apparatus is provided, which includes: a first photographic system having a first X-ray tube and a first X-ray detector; a second photographic system having a second X-ray tube and a second X-ray detector; a first supporting mechanism supporting the first photographic system; a second supporting mechanism supporting the second photographic system movably in a direction to come in close proximity to/move away from the first photographic system; and a control circuit controlling a movement of the second photographic system. The control circuit moves, at a command from an operator, the second photographic system selectively to one of a photographing position at which a photographic center axis crosses with the first photographic system, a evacuation position spaced apart from the photographing position, and a temporary evacuation position closer to the photographing position than the evacuation position is.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

One embodiment of an X-ray diagnostic apparatus according to the invention will now be described with reference to the accompanying drawings.

Figure 1:
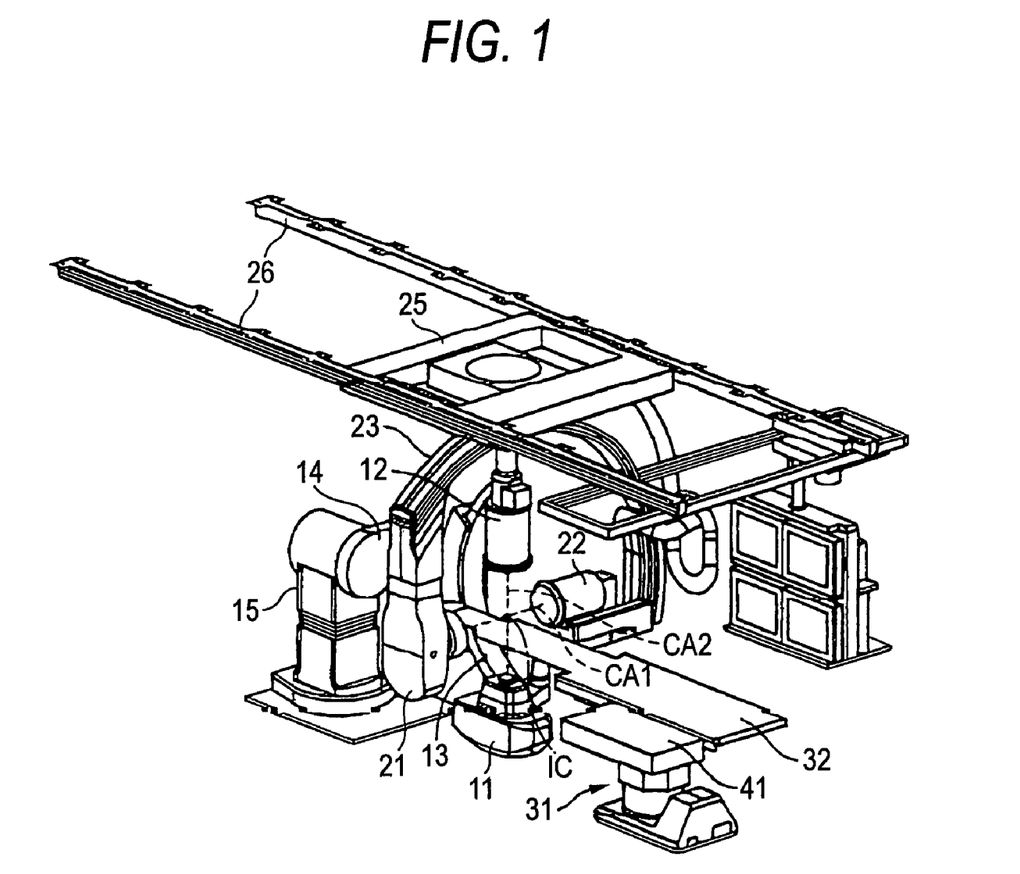
FIG. 1 is a view showing an outward appearance of an X-ray diagnostic apparatus according to one embodiment of the invention.
Figure 2:
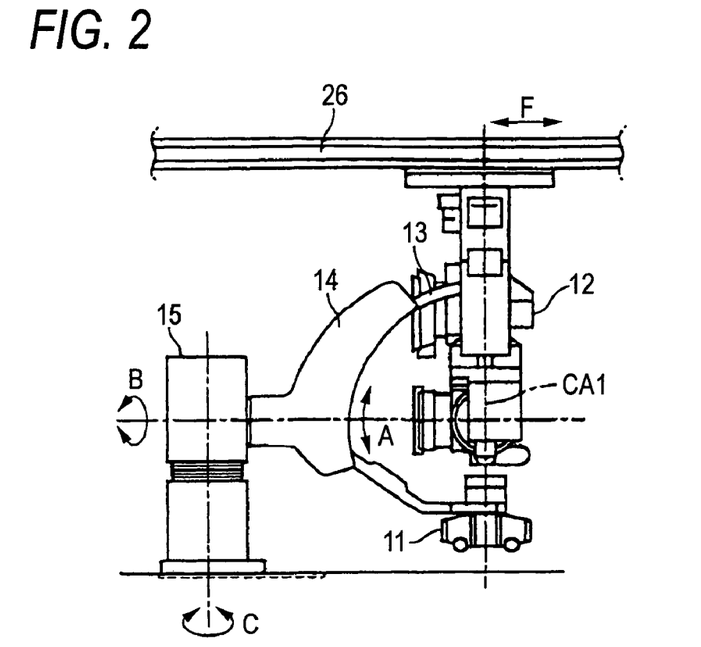
FIG. 2 is a side view of the X-ray diagnostic apparatus of FIG. 1.
Figure 3:
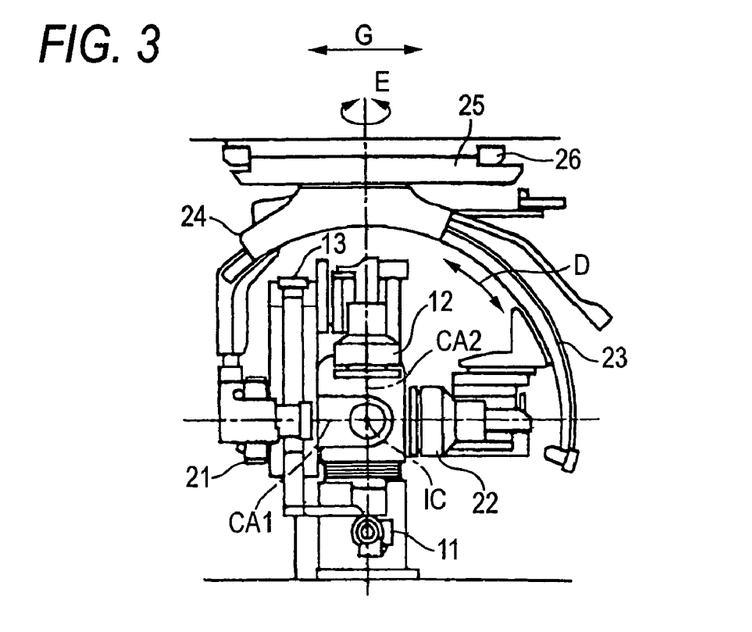
FIG. 3 is a front view of the X-ray diagnostic apparatus of FIG. 1.

FIG. 1 is a view showing an outward appearance of an X-ray diagnostic apparatus of this embodiment. FIG. 2 is a side view and FIG. 3 is a front view of the X-ray diagnostic apparatus. The X-ray diagnostic apparatus is of a biplane type, and is configured to include a frontal X-ray photographic system (first X-ray photographic system) and a lateral X-ray photographic system (second X-ray photographic system), so that a subject laid on a table top 32 of a diagnostic table 31 can be photographed in two directions simultaneously.

The frontal X-ray photographic system includes an X-ray tube 11 and an X-ray detector 12. The lateral X-ray photographic system includes an X-ray tube 21 and an X-ray detector 22. The X-ray detectors 12 and 22 adopt a combination of an image intensifier and a TV camera or a flat panel detector.

The X-ray tube 11 in the frontal system is attached to one end of a C-arm 13, and the X-ray detector 12 is attached to the other end of the C-arm 13. CA1 denotes a photographic center axis of the frontal photographic system, linking a focal point of the X-ray tube 11 and the center of an image-receiving plane of the X-ray detector 12. The X-ray tube 21 in the lateral system is attached to one end of an Ω-arm 23, and the X-ray detector 22 is attached to the other end of the Ω-arm 23. CA2 denotes a photographic center axis of the lateral photographic system, linking a focal point of the X-ray tube 21 and the center of an image-receiving plane of the X-ray detector 22. The photographic center axis CA1 of the frontal photographic system and the photographic center axis CA2 of the lateral photographic system cross with each other at a fixed point IC called an isocenter. Herein, the position of the frontal photographic system when the photographic center axis CA1 passes through the isocenter IC is referred to as the photographing position of the frontal photographic system. Likewise, the position of the lateral photographic system when the photographic center axis CA2 passes through the isocenter IC is referred to as the photographing position of the lateral photographic system.

The C-arm 13 in the frontal system is supported by a stand 15 installed to the floor, through an arm holder 14. The arm holder 14 holds the C-arm 13 slidably rotatable with respect to an arrow A. The stand 15 holds the arm holder 14 axially rotatable with respect to an arrow B. The stand 15 has a structure such that allows strut rotation (swiveling) with respect to an arrow C. This structure makes it possible to incline a photographic angle of the frontal X-ray photographic system arbitrarily with respect to the arrows A and B. Also, by allowing the swiveling with respect to the arrow C, it is possible to retract the frontal photographic system and the C-arm 13 from the photographing position.

The Ω-arm 23 in the lateral system is suspended from a ceiling base 25 through an arm holder 24. The arm holder 24 holds the Ω-arm 23 slidably rotatable with respect to an arrow D. The ceiling base 25 holds the arm holder 24 axially rotatable with respect to an arrow E. This structure makes it possible to incline a photographing angle of the lateral X-ray photographic system arbitrarily with respect to the arrows D and E. The ceiling base 25 is engaged with a traveling rail 26 laid on the ceiling surface, movably with respect to an arrow F or G. The traveling rail 26 has a sufficient longitudinal length having the isocenter IC at or nearly at the center. The lateral photographic system and the Ω-arm 23 are thus allowed to move in a broad range from a position in the vicinity of the end of the diagnostic table top 32 to the photographing position to a sufficiently remote position.

Figure 4:
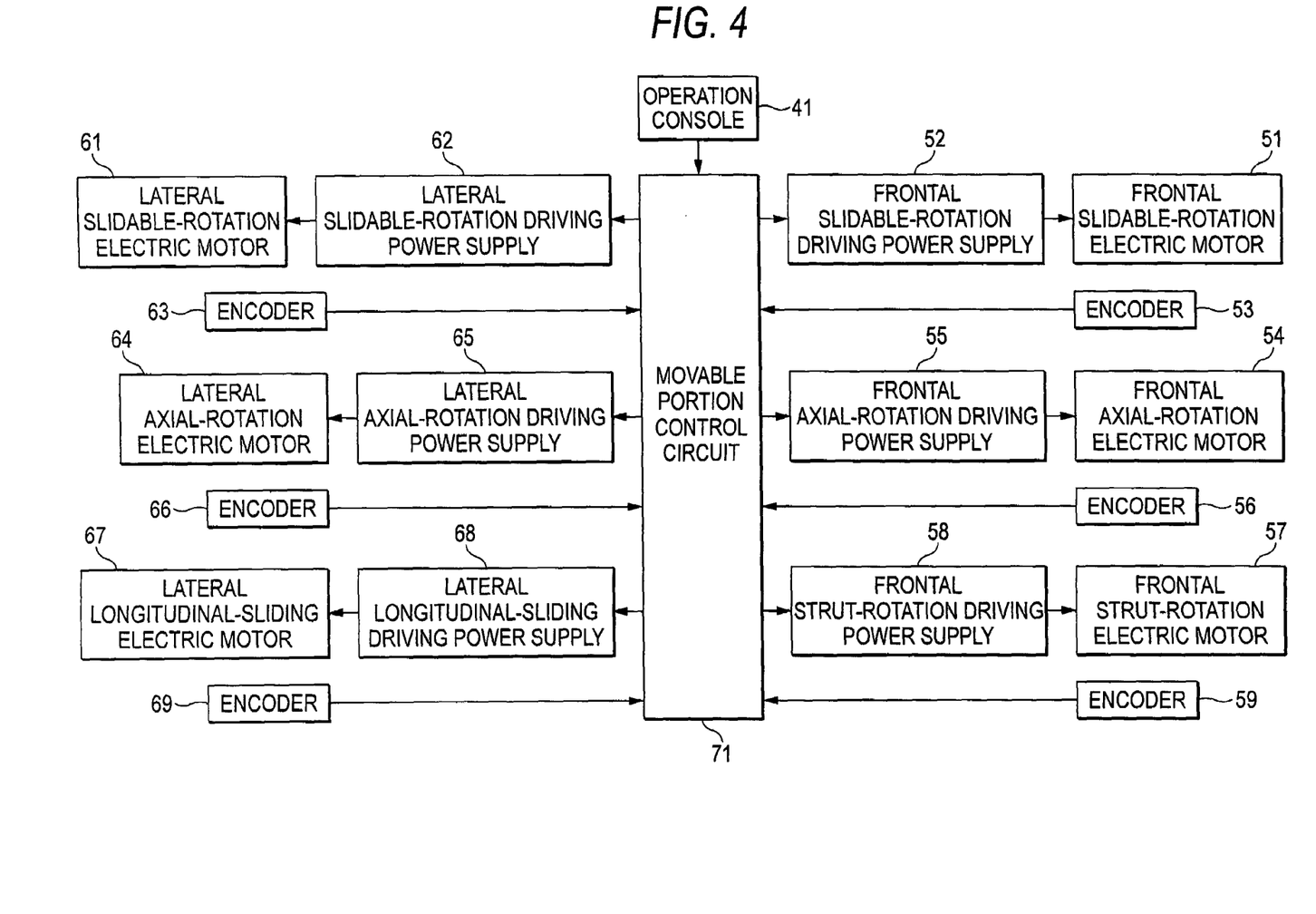
FIG. 4 is a control system diagram of movable portions in the X-ray diagnostic apparatus of FIG. 1.

Movements of movable portions A through G described above can be manipulated arbitrarily through an operation console 41 provided in close proximity to the diagnostic table 31. As shown in FIG. 4, a movable portion control circuit 71 is connected to the operation console 41. The respective movable portions are provided with electric motors 51, 54, 57, 61, 64, and 67 used to generate power needed for the movable portions, and power supplies 52, 55, 58, 62, 65, and 68 used to supply the respective electric motors with electric power. The movable portion control circuit 71 outputs an electric power supply control signal to any of the power supplies 52, 55, 58, 62, 65, and 68 corresponding to a specified movable portion at a command from the operator inputted through the operation console 41, and adjusts the control signal based on position signals from respective encoders 53, 56, 59, 63, 66, and 69. An arbitrary movable portion can be thus operated by an arbitrary quantity at a command from the operator.

Figure 5:
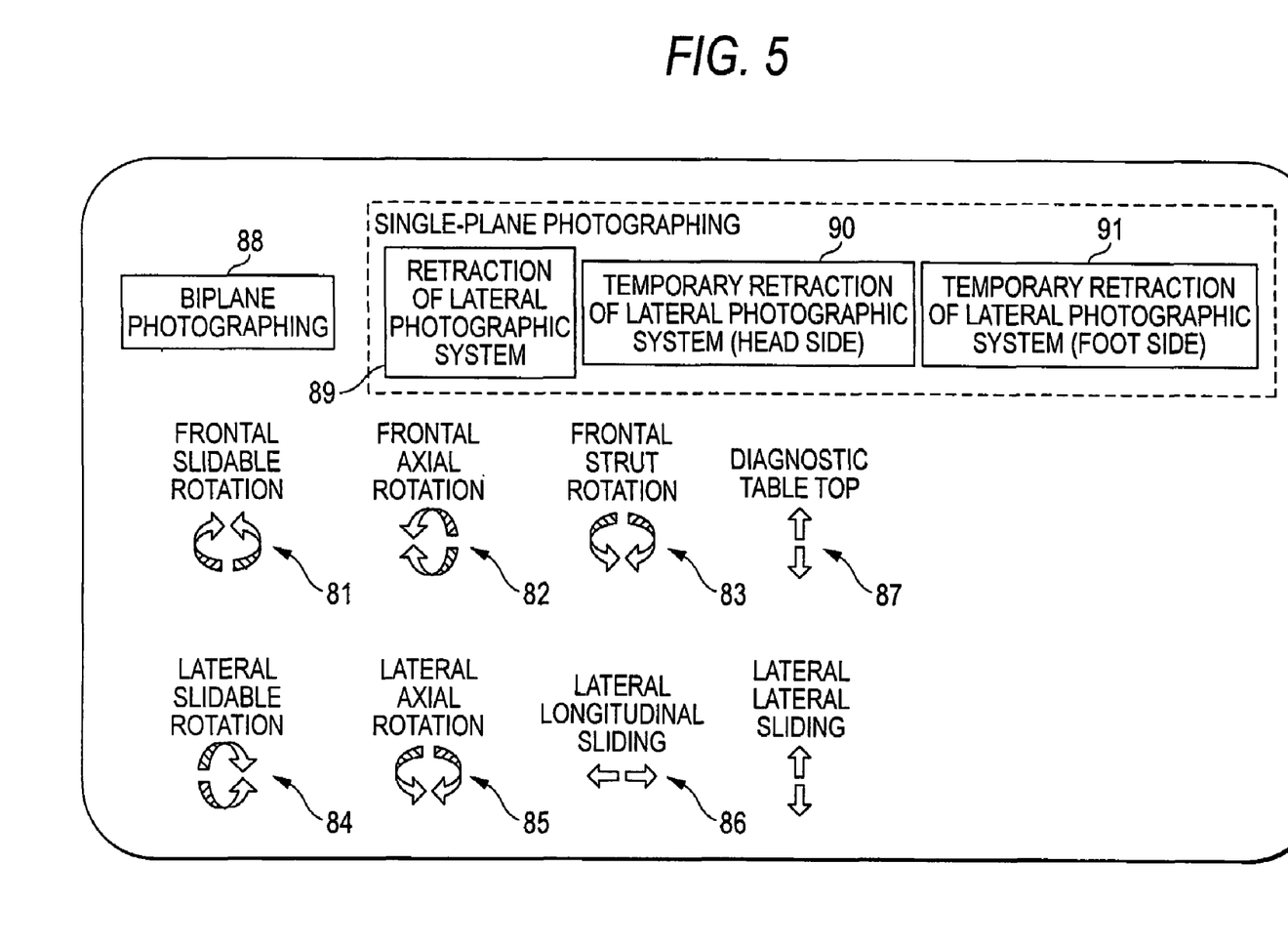
FIG. 5 is a view showing one example of an operation console of FIG. 4.

FIG. 5 is a view showing a control panel on the operation console 41. Respective operation buttons may comprise physical buttons or a touch panel. The operation console 41 is provided with an operation button 81 for forward/backward slidable rotation of the frontal system, an operation button 82 for forward/backward axial rotation of the frontal system, an operation button 83 for forward/backward strut rotation (swiveling) of the frontal system, an operation button 84 for forward/backward slidable rotation of the lateral system, an operation button 85 for forward/backward axial rotation of the lateral system, an operation button 86 for forward/backward longitudinal sliding of the lateral system, and an operation button 87 for horizontal and vertical movements of the table top 32. In addition to these buttons, a group of buttons to automatically move the lateral photographic system to a target position are provided, including an operation button 88 for biplane photographing, an operation button 89 for evacuation of the lateral photographic system, an operation button 90 for temporary evacuation of the lateral photographic system to the head side, and an operation button 91 for temporary evacuation of the lateral photographic system to the foot side. These buttons may not necessarily comprise exclusive-use buttons, and specific numbers may be assigned by using a ten-key numeric pad.

Explanations will now be given sequentially to sliding operations of the lateral photographic system under the control of the control circuit 71 upon manipulation of the operation button 88 for biplane photographing, the operation button 89 for evacuation of the lateral photographic system, the operation button 90 for temporary evacuation of the lateral photographic system to the head side, and the operation button 91 for temporary evacuation of the lateral photographic system to the foot side.

Figure 6:
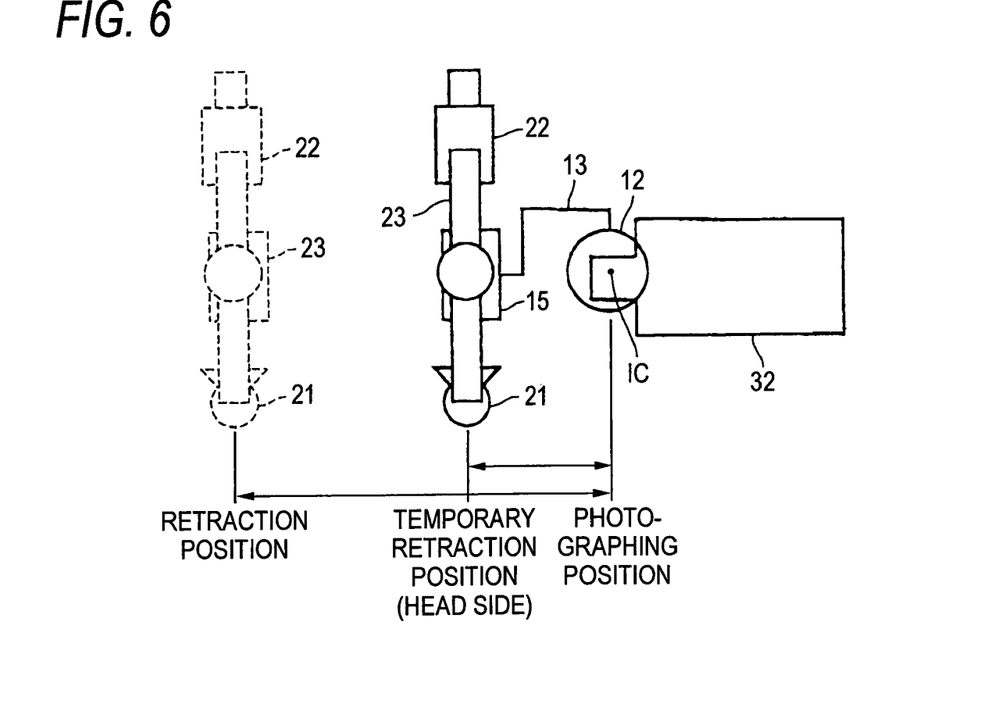
FIG. 6 is a plan view showing a temporary evacuation position on the head side of a lateral photographic system of FIG. 1.

Initially, when the operation button 89 for evacuation of the lateral photographic system is pressed, the control circuit 71 supplies a control signal to the power supply 68 corresponding to the longitudinal sliding of the lateral photographic system, so that, as indicated by a dotted line of FIG. 6, the lateral photographic system, the Ω-arm 23, etc. are moved to and halted at the evacuation position sufficiently remote from the frontal photographic system located at the photographing position.

When the operation button 88 for biplane photographing is pressed, the control circuit 71 supplies a control signal to the power supply 68 corresponding to the longitudinal sliding of the lateral photographic system, so that the lateral photographic system, the Ω-arm 23, etc. are moved to and halted at the photographing position at which the photographic center axis CA2 of the lateral photographic system crosses with the photographic center axis CA1 of the frontal photographic system at the isocenter IC.

When the operation button 90 for temporary evacuation of the lateral photographic system to the head side is pressed, the control circuit 71 supplies a control signal to the power supply 68 corresponding to the longitudinal sliding of the lateral photographic system, so that, as shown in FIG. 6, the lateral photographic system, the Ω-arm 23, etc. are moved to and halted at a first temporary evacuation position. Also, when the operation button 90 for temporary evacuation of the lateral photographic system to the head side is pressed and the lateral photographic system has reached the temporary evacuation position, the control circuit 71 cancels a disable state of the frontal photographic system.

The first temporary evacuation position is located somewhere between the evacuation position and the photographing position. The first temporary evacuation position is closer to the photographing position than the evacuation position is. The first temporary evacuation position is set to a position at which the lateral photographic system, the Ω-arm 23, etc. are in the closest proximity to the photographing position without interfering with movements of the frontal photographic system located at the photographing position, including slidable rotation and axial rotation but excluding swiveling, and typically, as shown in FIG. 6, it is set to a position at which the lateral photographic system and the Ω-arm 23 come over above the stand 15 of the frontal photographic system.

Figure 7:
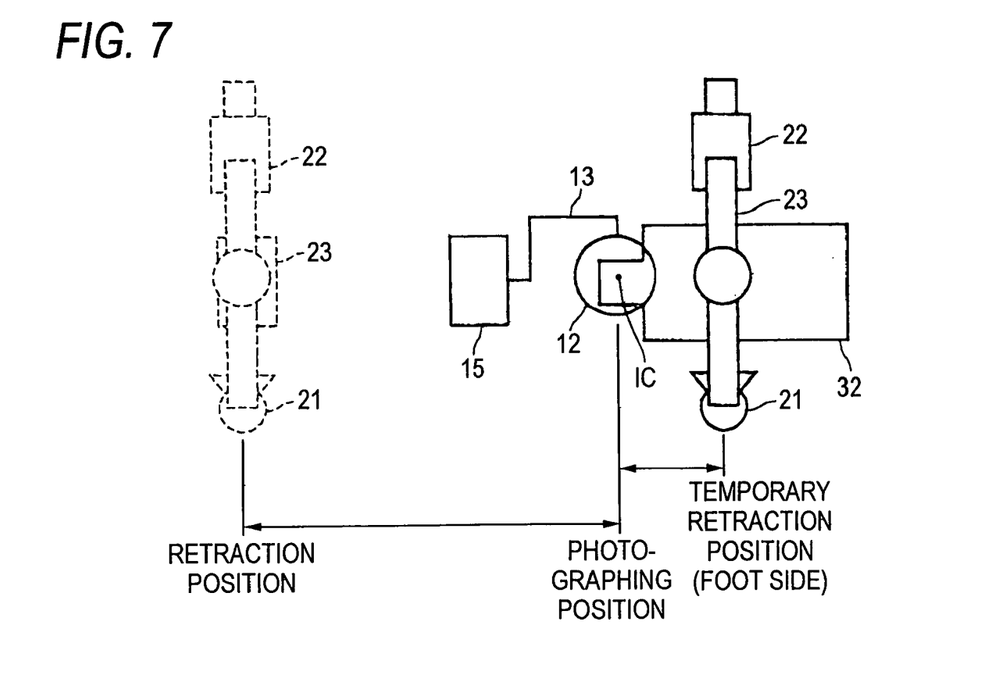
FIG. 7 is a plan view showing a temporary evacuation position on the foot side of the lateral photographic system of FIG. 1.

When the operation button 91 for temporary evacuation of the lateral photographic system to the foot side is pressed, the control circuit 71 supplies a control signal to the power supply 68 corresponding to the longitudinal sliding of the lateral photographic system, so that, as shown in FIG. 7, the lateral photographic system, the Ω-arm 23, etc. are moved to and halted at a temporary evacuation position (second temporary evacuation position), which is on the opposite side of the evacuation position with the photographing position in between and is closer to the photographing position than the evacuation position is. Also, when the operation button 91 for temporary evacuation of the lateral photographic system to the foot side is pressed and the lateral photographic system has reached the temporary evacuation position, the control circuit 71 cancels a disable state of the frontal photographic system.

The second temporary evacuation position is on the opposite side of the evacuation position with the photographing position in between, and is closer to the photographing position than the evacuation position is. The second temporary evacuation position is set to a position at which the lateral photographic system, the Ω-arm 23, etc. are in the closest proximity to the photographing position without interfering with the movements of the frontal photographic system located at the photographing position, including swiveling, slidable rotation, and axial rotation, and typically, as shown in FIG. 7, it is set to a position at which the lateral photographic system and the Ω-arm 23 come over above the center or nearly the center of the table top 32.

It should be noted that the control circuit 71 is furnished with an operation restricting function. This function restricts operations to ensure safety and to avoid physical collision between the frontal photographic system and C-arm 13 and the lateral photographic system and Ω-arm 23. More specifically, while the lateral photographic system and the Ω-arm 23 are located at the photographing position, the control circuit 71 allows slidable rotation and axial rotation of the frontal photographic system and the C-arm 13, but inhibits an operation (electric operation) inducing strut rotation (swiveling). Meanwhile, the control circuit 71 allows all the movements of the lateral photographic system and the Ω-arm 23. Also, while the lateral photographic system and the Ω-arm 23 are located at the evacuation position, the control circuit 71 allows all the operations of the frontal photographic system and the C-arm 13, including strut rotation (swiveling), slidable rotation, and axial rotation, and inhibits all the operations of the lateral photographic system and the Ω-arm 23.

While the lateral photographic system and the Ω-arm 23 are located at the temporary evacuation position on the head side, the control circuit 71 allows slidable rotation and axial rotation of the frontal photographic system and the C-arm 13, but inhibits an operation inducing strut rotation (swiveling). Meanwhile, the control circuit 71 allows all the movements of the lateral photographic system and the Ω-arm 23. While the lateral photographic system and the Ω-arm 23 are located at the temporary evacuation position on the foot side, the control circuit 71 allows all the operations (electric operations) of the frontal photographic system and the C-arm 13, including strut rotation (swiveling), slidable rotation, and axial rotation, and inhibits all the operations of the lateral photographic system and the Ω-arm 23.

Further, while the lateral photographic system and the Ω-arm 23 are located at a position other than the photographing position, the evacuation position, the temporary evacuation position on the head side, and the temporary evacuation position on the foot side, the control circuit 71 inhibits all the operations of the frontal photographic system and the C-arm 13, including slidable rotation, axial rotation, and strut rotation (swiveling).

As has been described, according to this embodiment, the lateral photographic system, the Ω-arm 23, etc. can be retracted temporarily to the temporary evacuation position, which is closer to the photographing position than the evacuation position is and at which the lateral photographic system interferes with neither slidable rotation nor axial rotation of the frontal photographic system located at the photographing position. It is thus possible to shorten a travel distance of the lateral photographic system and the Ω-arm 23 associated with the switching between biplane photographing and single-plane photographing, and the stand-by time can be shortened as a result. Also, by providing two temporary evacuation positions on the head and foot sides, respectively, the temporary evacuation position whichever is the more appropriate in preventing the interference with an examination or an operation work can be chosen. Further, because the movement to either temporary evacuation position and the returning to the biplane photographing position can be specified by a single button operation, ease of use is enhanced satisfactorily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
   a first photographic system having a first X-ray tube and a first X-ray detector;
   a second photographic system having a second X-ray tube and a second X-ray detector;
   a first supporting mechanism supporting said first photographic system;

a second supporting mechanism supporting said second photographic system movably in a direction to come in close proximity to/move away from said first photographic system; and a control circuit controlling a movement of said second photographic system, wherein, when a first operator instruction is inputted, said control circuit automatically moves said second photographic system to a photography position where said first photographic system and a photography center axis cross, when a second operator instruction is inputted, said control circuit automatically moves said second photographic system to a predetermined evacuation position distant from said photography position, and when a third operator instruction is inputted, said control circuit automatically moves said second photographic system to a predetermined temporary evacuation position closer to said photography position, than said predetermined evacuation position, and wherein when said second photographic system is moved to said predetermined temporary evacuation position, said second photographic system is maintained at said predetermined temporary evacuation position until said control circuit receives a subsequent operator instruction.

2. The X-ray diagnostic apparatus according to claim 1, wherein said predetermined temporary evacuation position is located between said photographing position and said predetermined evacuation position.

3. The X-ray diagnostic apparatus according to claim 1, wherein said photographing position is located between said predetermined evacuation position and said predetermined temporary evacuation position.

4. The X-ray diagnostic apparatus according to claim 1, further comprising an operation portion having a button corresponding to a movement of said second photographic system to said photographing position, a button corresponding to a movement of said second photographic system to said predetermined evacuation position, and a button corresponding to a movement of said second photographic system to said predetermined temporary evacuation position.

5. The X-ray diagnostic apparatus according to claim 1, wherein:

said first supporting mechanism has a floor-standing stand and a C-arm;

said second supporting mechanism has a ceiling traveling rail, a strut suspended from said ceiling traveling rail, and an Ω-arm attached to a lower end of said strut; and said predetermined temporary evacuation position is a position at which said Ω-arm comes over above said floor-standing stand.

6. The X-ray diagnostic apparatus according to claim 1, further comprising a diagnostic table on which a subject is laid, wherein:

said first supporting mechanism has a floor-standing stand and a C-arm;

said second supporting mechanism has a ceiling traveling rail, a strut suspended from said ceiling traveling rail, and an Ω-arm attached to a lower end of said strut; and said predetermined temporary evacuation position is a position at which said Ω-arm comes over above a center or nearly the center of said diagnostic table.

7. The X-ray diagnostic apparatus according to claim 1, wherein:

said first supporting mechanism has a floor-standing stand and a C-arm supported by said stand in such a manner that swiveling, axial rotation, and slidable rotation are allowed;

said second supporting mechanism has a ceiling traveling rail, a strut suspended from said ceiling traveling rail, and an Ω-arm attached to a lower end of said strut; and said second photographic system, located at said predetermined temporary evacuation position, together with said (Ω-arm does not interfere with movements including the axial rotation and the slidable rotation but excluding the swiveling.

8. The X-ray diagnostic apparatus according to claim 7, wherein, while said second photographic system is located at said predetermined evacuation position, said control circuit allows the swiveling, the axial rotation, and the slidable rotation, and while said second photographic system is located at one of said photographing position and said predetermined temporary evacuation position, said control circuit inhibits the swiveling but allows the axial rotation and the slidable rotation.

9. The X-ray diagnostic apparatus according to claim 1, wherein when said second photographic system is being moved to said predetermined evacuation position, said control circuit places said first photographic system in a disable state, and when said second photographic system reaches said predetermined temporary evacuation position, said control circuit cancels the disable state of said first photographic system.

10. An X-ray diagnostic apparatus, comprising:

a first photographic system having a first X-ray tube and a first X-ray detector;

a second photographic system having a second X-ray tube and a second X-ray detector;

a first supporting mechanism supporting said first photographic system;

a second supporting mechanism supporting said second photographic system movably in a direction to come in close proximity to/move away from said first photographic system; and a control circuit controlling a movement of said second photographic system, wherein, when a first operator instruction is inputted, said control circuit automatically moves said second photographic system to a photography position where said first photographic system and a photography center axis cross, when a second operator instruction is inputted, said control circuit automatically moves said second photographic system to a predetermined evacuation position distant from said photography position, when a third operator instruction is inputted, said control circuit automatically moves said second photographic system to a first predetermined temporary evacuation position closer to said photography position than said predetermined evacuation position, and when a fourth operator instruction is inputted, said control circuit automatically moves said second photographic system to a second predetermined temporary evacuation position, and wherein when said second photographic system is moved to said first predetermined temporary evacuation position, said second photographic system is maintained at said predetermined temporary evacuation position until said control circuit receives a subsequent operator instruction.

11. The X-ray diagnostic apparatus according to claim 10, wherein:
said first supporting mechanism has a floor-standing stand and a C-arm;
said second supporting mechanism has a ceiling traveling rail, a strut suspended from said ceiling traveling rail, and an Ω-arm attached to a lower end of said strut; and
said first predetermined temporary evacuation position is a position at which said Ω-arm comes over above said floor-standing stand.

12. The X-ray diagnostic apparatus according to claim 10, further comprising a diagnostic table on which a subject is laid, wherein:
said first supporting mechanism has a floor-standing stand and a C-arm;
said second supporting mechanism has a ceiling traveling rail, a strut suspended from said ceiling traveling rail, and an Ω-arm attached to a lower end of said strut; and
said second predetermined temporary evacuation position is a position at which said Ω-arm comes over above a center or nearly the center of said diagnostic table.

13. The X-ray diagnostic apparatus according to claim 10, further comprising an operation portion having a button corresponding to a movement of said second photographic system to said photographing position, a button corresponding to a movement of said second photographic system to said predetermined evacuation position, a button corresponding to a movement of said second photographic system to said first predetermined temporary evacuation position, and a button corresponding to a movement of said second photographic system to said second predetermined temporary evacuation position.

14. The X-ray diagnostic apparatus according to claim 10, wherein when said second photographic system is being moved to said first predetermined temporary evacuation position or said second predetermined temporary evacuation position, said control circuit places said first photographic system in a disable state, and when said second photographic system reaches said first predetermined temporary evacuation position or said second predetermined temporary evacuation position, said control circuit cancels a disable state of said first photographic system.

15. An X-ray diagnostic apparatus, comprising:
a first photographic system having a first X-ray tube and a first X-ray detector;
a second photographic system having a second X-ray tube and a second X-ray detector;
a first supporting mechanism supporting said first photographic system; and
a second supporting mechanism supporting said second photographic system movably; and
a control circuit configured to move said second photographic system,
wherein,
when a first operator instruction is inputted, said control circuit automatically moves said second photographic system to a photography position where said first photographic system and a photography center axis cross,
when a second operator instruction is inputted, said control circuit automatically moves said second photographic system to a predetermined evacuation position distant from said photography position, and
when a third operator instruction is inputted, said control circuit automatically moves said second photographic system to a predetermined temporary evacuation position closer to said photography position than said predetermined evacuation position, according to a corresponding operator instruction; and
wherein when said second photographic system is moved to said predetermined temporary evacuation position, said second photographic system is maintained at said predetermined temporary evacuation position until said control circuit receives a subsequent operator instruction.

16. The X-ray diagnostic apparatus according to claim 15, wherein said predetermined temporary evacuation position is located between said photographing position and said predetermined evacuation position.

17. The X-ray diagnostic apparatus according to claim 15, wherein said photographing position is located between said predetermined evacuation position and said predetermined temporary evacuation position.

18. The X-ray diagnostic apparatus according to claim 15, further comprising an operation portion having a button corresponding to a movement of said second photographic system to said photographing position, a button corresponding to a movement of said second photographic system to said predetermined evacuation position, and a button corresponding to a movement of said second photographic system to said predetermined temporary evacuation position.

19. The X-ray diagnostic apparatus according to claim 15, wherein when said second photographic system is being moved to said predetermined evacuation position, said control circuit places said first photographic system in a disable state, and when said second photographic system reaches said predetermined temporary evacuation position, said control circuit cancels a disable state of said first photographic system.

* * * * *